United States Patent [19]
Rice

[11] Patent Number: 5,144,944
[45] Date of Patent: Sep. 8, 1992

[54] SKIN CLOSURE DRESSING FOR EYELIDS
[75] Inventor: Charles D. Rice, Little Rock, Ark.
[73] Assignee: University of Arkansas, Little Rock, Ark.
[21] Appl. No.: 512,274
[22] Filed: Apr. 20, 1990
[51] Int. Cl.⁵ .............................................. A61F 13/12
[52] U.S. Cl. ........................................ 602/74; 602/41; 606/214; 606/215
[58] Field of Search ................................ 128/155–156, 128/163, 82, 106.1, 107.1, 112.1; 602/41, 42, 74; 606/204, 214, 215

[56] References Cited
U.S. PATENT DOCUMENTS 3,687,136 8/1972 Carmody .............................. 128/156
4,630,603 12/1986 Greenway ............................ 128/156
4,867,150 9/1989 Gilbert ................................. 128/156

Primary Examiner—Randall L. Green
Assistant Examiner—Gina M. Gualtieri
Attorney, Agent, or Firm—Hermann Ivester

[57] ABSTRACT

A skin closure dressing for eyelids comprising a thin backing material, a layer of adhesive on one face of the backing material, a multi-layer pad covering a portion of the face of the backing material, at least one of the layers of the multi-layer pad being an absorbent material, and an outer layer of the multi-layer pad being a non-adhesive material. The dressing is thin and narrow enough to not cause occlusion of the eye. A pair of side tabs are provided to assist in removal of the dressing.

10 Claims, 1 Drawing Sheet

U.S. Patent  Sep. 8, 1992  5,144,944
FIG. 1
FIG. 2
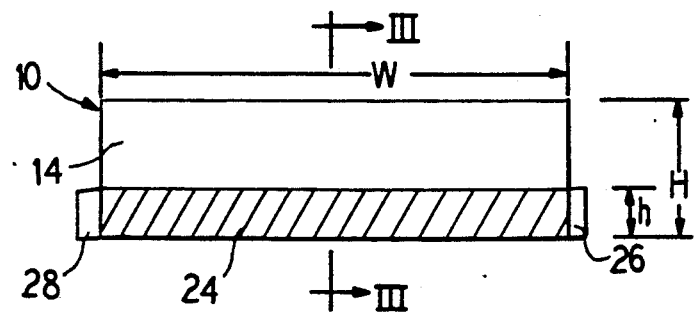
FIG. 3
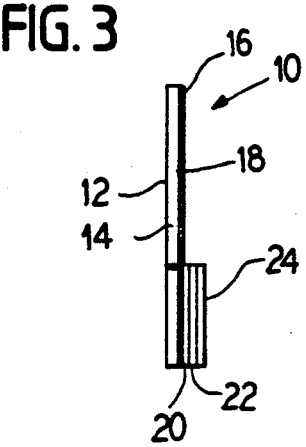
FIG. 4
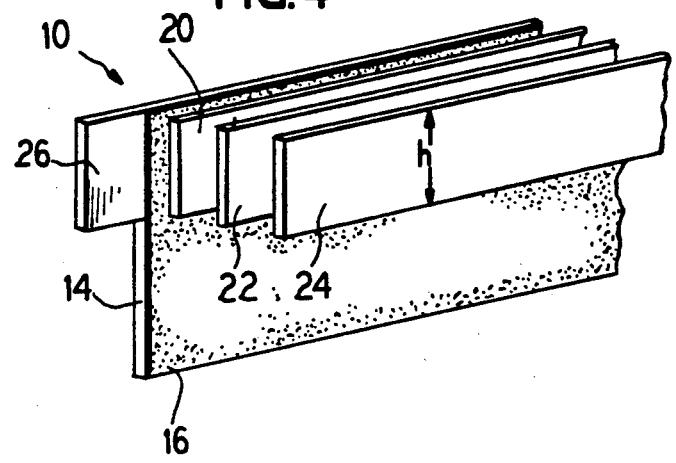

SKIN CLOSURE DRESSING FOR EYELIDS

BACKGROUND OF THE INVENTION

The invention relates to skin closure dressings and more particularly to a skin closure dressing for use on an eyelid. Specific skin closure dressings suitable for eyelid incisions are not commercially available. Conventional dressings are too large or restrictive for the delicate incisions of the mobile eyelids. Presently, after eyelid surgery is performed, such as blepharoplasty, ptosis, and reconstructive surgery, the wound is either left uncovered or covered with an occlusive dressing and tape. The uncovered wound often oozes blood or serous material which is bothersome to the patient. The occlusive dressings, generally comprise cotton eye pads which are commonly taped to the lid area, are often too bulky for use on the mobile eyelid.

SUMMARY OF THE INVENTION

The present invention provides a thin and comfortable dressing for eyelids which contains both an adhesive and a non-adhesive side on one face of the dressing. The non-adhesive surface absorbs the small amount of blood from the incision line and prevents wound separation or discomfort when the dressing is removed. The adhesive component allows the dressing to adhere to the eyelid but is small enough so as not to occlude vision or interfere with normal eyelid movement. In the upper lid, the adhesive component is positioned above the incision site and in the lower lid, the adhesive side is positioned below the incision. As a result of the use of such a dressing, a much cleaner wound results, since small clots do not adhere to the skin surface or sutures. The dressing itself comprises an adhesive (water repellant) backing with a non-adherent surface to contact the incision line. The non-adherent portion contains three layers, the outside layers are non-adhesive and the central area is absorbent. The absorbent layer promotes clot formation which prevents any further oozing from the incision line. The non-adhesive surface prevents blood clots from adhering to the wound at the time of dressing removal.

BRIEF DESCRIPTION OF THE DRAWINGS

FIG. 1 is a front elevational view of the dressing placed on a patient's upper eyelid.

FIG. 2 is a front elevational view of the dressing.

FIG. 3 is a side sectional view of the dressing taken generally along the lines III—III of FIG. 2.

FIG. 4 is a partial, exploded view illustrating the various layers of the dressing.

DETAILED DESCRIPTION OF THE PREFERRED EMBODIMENTS

The present invention provides a skin closure dressing shown generally at 10 in the figures for use particularly on eyelids. In FIG. 1, the dressing 10 is illustrated in place on a patient's upper eyelid E. The dressing 10 is shown in greater detail in FIGS. 2-4 where it is seen that a front face 12 of the dressing is planar and constitutes a thin backing member 14 having an adhesive material layer 16 applied to a back face 18 thereof. Preferably the adhesive is waterproof. The thickness of the backing layer is preferably in the range of 50-300 microns.

A portion of a height H of the backing 14 is covered by a triple-layer pad composed of layers 20, 22 and 24 as best seen in FIG. 4. The central layer 22 is an absorbent layer and can be formed of a material such as cotton-acrylic. The two outer layers 20, 24 are non-adhesive and may comprise a polyurethane coating. Such a coating would permit passage of liquids such as blood and serous material. By providing the non-adhesive surface layer 24, which will be placed against the incision line, any blood or serous material which has oozed from the incision will pass through the outer layer 24 and will be absorbed by the central layer 22 thus preventing any adhesion between the dressing 10 and the incision line.

As best seen in FIG. 2, small tabs 26, 28 are provided at each lateral end of the dressing 10 which have a height h approximately equal to a height h of the layers 20, 22 and 24. The height of the dressing may be in the range of 5-15 mm and the height h of the tabs and layers should be approximately half of the height H. These end tabs are provided to assist in the removal of the dressing by providing a portion which does not have adhesive thereon and which will be slightly spaced away from the surface of the eyelid when the dressing is in place. These tabs thus will assist in the lifting of the dressing away from the eyelid.

Due to the compact size of the dressing, being both thin and narrow, the dressing will not interfere with normal eyelid movement. The thickness of the dressing, including the layers 20, 22 and 24 should preferably be in the range of 500-1500 microns. It is clearly shown in FIG. 1 that the height H of the backing is shorter than a height of the eyelid. Also, the height H of the backing is relatively shorter than a width W. The width W may be in the range of 2-4 cm. However, the dressing will result in a much cleaner wound by absorbing any material oozing from the incision line and by preventing such material from clotting on the eyelid at the incision line or to the sutures. Further, due to the use of the non-adherent layer 24, removal of the dressing does not result in any discomfort to the patient since the only adherence of the dressing to the eyelid is the relatively narrow exposed adhesive layer 16 which is positioned so as to be displaced from the incision line.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. A skin closure dressing for eyelids comprising:
    a thin backing material with a height dimension substantially smaller than a perpendicular width dimension;
    a layer of adhesive on one face of said backing material;
    a multi-layer pad covering a portion of said face of said backing material, said multi-layer pad having a width dimension substantially equal to said width dimension of said backing material and a height dimension less than said height dimension of said backing material;
    at least one of said layers of said multi-layer pad being an absorbent material; and
    an outer layer of said multi-layer pad being a non-adhesive material.

2. A skin closure dressing according to claim 1, wherein said absorbent material is a cotton-acrylic blend.

3. A skin closure dressing according to claim 1, wherein said non-adhesive material is polyurethane.

4. A skin closure dressing according to claim 1, wherein said backing material includes small tabs projecting at each lateral side, extending beyond said width dimension of said backing material, said tabs not having adhesive thereon and having a height dimension corresponding generally to said height dimension of said multi-layer pad.

5. A skin closure dressing according to claim 1, wherein said multi-layer pad comprises three layers, a middle of said layers being said absorbent material.

6. A skin closure dressing for eyelids comprising:
- a sheet of backing material having a height relatively shorter than a width;
- a layer of adhesive on one face of said backing material;
- a triple-layer pad covering a portion of said face of said backing material said triple-layer pad having a width substantially equal to said width of said backing material and a height less than said height of said backing material;
- a central one of said layers of said triple-layer pad being an absorbent material; and
- an outer layer of said triple-layer pad being a non-adhesive material.

7. A skin closure dressing according to claim 6, wherein said absorbent material is a cotton-acrylic blend.

8. A skin closure dressing according to claim 6, wherein said non-adhesive material is polyurethane.

9. A skin closure dressing according to claim 6, wherein said backing material includes small tabs projecting at each lateral side, extending beyond said width of said backing material, said tabs not having adhesive thereon and having a height corresponding generally to said height of said triple-layer pad.

10. A skin closure dressing for eyelids comprising:
- a sheet of thin backing material having a height relatively shorter than a width;
- a layer of adhesive covering one face of said backing material;
- a thin triple-layer pad covering only a portion of said height of said backing material on said face and extending along an entire edge of said backing material to cover the entire width of said backing material;
  - said backing material including small tabs projecting at each lateral side, extending beyond said width of said backing material, said tabs not having adhesive thereon and having a height corresponding to the height of said triple-layer pad;
- a central one of said layers of said triple-layer pad being a cotton-acrylic blend material; and
- an outer layer of said triple-layer pad being a polyurethane coating.

* * * * *